(12) United States Patent
Nzeadibe et al.

(10) Patent No.: US 9,297,734 B2
(45) Date of Patent: Mar. 29, 2016

(54) APPARATUS AND METHOD TO TEST A PROPERTY OF A FLUID

(75) Inventors: Kingsley Ihueze Nzeadibe, Houston, TX (US); Kenneth Heidt Matthews, III, Kingwood, TX (US); Dale Eugene Jamison, Humble, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 181 days.

(21) Appl. No.: 13/557,570

(22) Filed: Jul. 25, 2012

(65) Prior Publication Data

US 2014/0026645 A1    Jan. 30, 2014

(51) Int. Cl.
*G01N 11/10* (2006.01)
*G01N 11/12* (2006.01)

(52) U.S. Cl.
CPC ............... *G01N 11/10* (2013.01); *G01N 11/12* (2013.01)

(58) Field of Classification Search
CPC ............................... G01N 11/10; G01N 11/12
See application file for complete search history.

(56) References Cited

U.S. PATENT DOCUMENTS

| 2,625,034 | A | * | 1/1953 | Patterson, Jr. | ............... 73/54.23 |
| 2,747,399 | A | | 5/1956 | Foreman | |
| 5,082,135 | A | | 1/1992 | Decoster | |
| 6,213,777 | B1 | * | 4/2001 | Seitzinger | ................... 433/229 |

FOREIGN PATENT DOCUMENTS

FR     23817447 A7    9/1978
JP     05079967 A  *  3/1993

OTHER PUBLICATIONS

Fann Shearometer Tube (Weighted) Instruction Card (2007).
International Search Report and Written Opinion issued in PCT Application No. PCT/US2013/050667 mailed Jul. 7, 2014, 11 pages.
International Preliminary Report on Patentability issued in PCT Application No. PCT/US2013/050667 mailed Jan. 27, 2015, 7 pages.
Patent Examination Report No. 1 issued in related Australian Patent Application No. 2013293396 issued Aug. 13, 2015, 3 pages.

* cited by examiner

*Primary Examiner* — Paul West
(74) *Attorney, Agent, or Firm* — Scott H. Brown; Baker Botts L.L.P.

(57) ABSTRACT

An apparatus to test a property of a fluid is provided. The apparatus includes a suspended member to be submerged in a fluid and a control device. The control device is coupled to the suspended member and is configured to pull the suspended member through at least a portion of the fluid to test a property of the fluid.

19 Claims, 7 Drawing Sheets

APPARATUS AND METHOD TO TEST A PROPERTY OF A FLUID

BACKGROUND

The present disclosure relates generally to measuring fluid properties and, more particularly, to an apparatus and method to test a property of a fluid.

Drilling fluids are commonly used when drilling a wellbore which penetrates one or more subterranean earth formations. The shear strength of a drilling fluid is an important drilling fluid property, the knowledge of which may indicate drilling fluid that will be stable in a wellbore after a long period of time. Conventional methods of determining shear strength may involve the use of a shear tube on top of a column of test fluid. For a fragile or low shear strength test fluid, the weight of the shear tube may be sufficient for the shear tube to break the surface of the test fluid and move into the column. However, if the test fluid surface holds the weight of the shear tube, weight is incrementally added to the shear tube to ensure movement of the shear tube past the surface and into the column of test fluid. Impact loading from the process of adding weight to the shear tube can vary the measurement reading. In general, conventional methods of determining shear strength are prone to variability in measurements and human error; measurement repeatability and accuracy is difficult to achieve.

Needed in the art are apparatuses and methods to measure properties of a fluid that are more reliable and easier to implement, and that enable greater repeatability and accuracy.

SUMMARY

The present disclosure relates generally to measuring fluid properties and, more particularly, to an apparatus and method to test a property of a fluid.

In one aspect, an apparatus to test a property of a fluid is disclosed. The apparatus includes a suspended member to be submerged in a fluid and a control device. The control device is coupled to the suspended member and is configured to pull the suspended member through at least a portion of the fluid to test a property of the fluid.

In another aspect, an apparatus to test a property of a fluid is disclosed where the apparatus includes a container comprising a cavity and a catch adjacent to the cavity. The apparatus also includes a crosspiece adapted to span at least a portion of the cavity. A suspended member is coupled to the crosspiece so that the suspended member is disposed within the cavity when the crosspiece is seated against the catch and so that the suspended member is pulled through at least a portion of the cavity when the crosspiece is lifted from the catch.

In yet another aspect, a method of testing a property of a fluid is disclosed. The method includes introducing a fluid into a container, disposing at least a portion of a suspended member in the fluid, and pulling the suspended member through at least a portion of the fluid. The property of the fluid is based, at least in part, on the pulling of the suspended member through at least the portion of the fluid.

Accordingly, certain embodiments according to the present disclosure, as compared to conventional means, may allow for significantly increased reliability, ease of use, repeatability and accuracy. Certain embodiments may allow for multiple simultaneous measurements with multiple units. Certain embodiments may be portable and adaptable to different testing setup areas. The features and advantages of the present disclosure will be readily apparent to those skilled in the art. While numerous changes may be made by those skilled in the art, such changes are within the spirit of the disclosure.

BRIEF DESCRIPTION OF THE DRAWINGS

Some specific exemplary embodiments of the disclosure may be understood by referring, in part, to the following description and the accompanying drawings.

While embodiments of this disclosure have been depicted and described and are defined by reference to exemplary embodiments of the disclosure, such references do not imply a limitation on the disclosure, and no such limitation is to be inferred. The subject matter disclosed is capable of considerable modification, alteration, and equivalents in form and function, as will occur to those skilled in the pertinent art and having the benefit of this disclosure. The depicted and described embodiments of this disclosure are examples only, and not exhaustive of the scope of the disclosure.

DETAILED DESCRIPTION

The present disclosure relates generally to measuring fluid properties and, more particularly, to an apparatus and method to test a property of a fluid.

Illustrative embodiments of the present disclosure are described in detail herein. In the interest of clarity, not all features of an actual implementation may be described in this specification. It will of course be appreciated that in the development of any such actual embodiment, numerous implementation specific decisions must be made to achieve the specific implementation goals, which will vary from one implementation to another. Moreover, it will be appreciated that such a development effort might be complex and time consuming, but would nevertheless be a routine undertaking for those of ordinary skill in the art having the benefit of the present disclosure. To facilitate a better understanding of the present disclosure, the following examples of certain embodiments are given. In no way should the following examples be read to limit, or define, the scope of the disclosure.

Certain embodiments of the present disclosure may provide apparatuses and methods to test a property of a fluid. In certain embodiments, the property may be one or both of a shear strength and a gel strength. In certain embodiments, the apparatuses and methods may test a property of a fluid, at least in part, by pulling a suspended member through at least a portion of the fluid.

Figure 1:
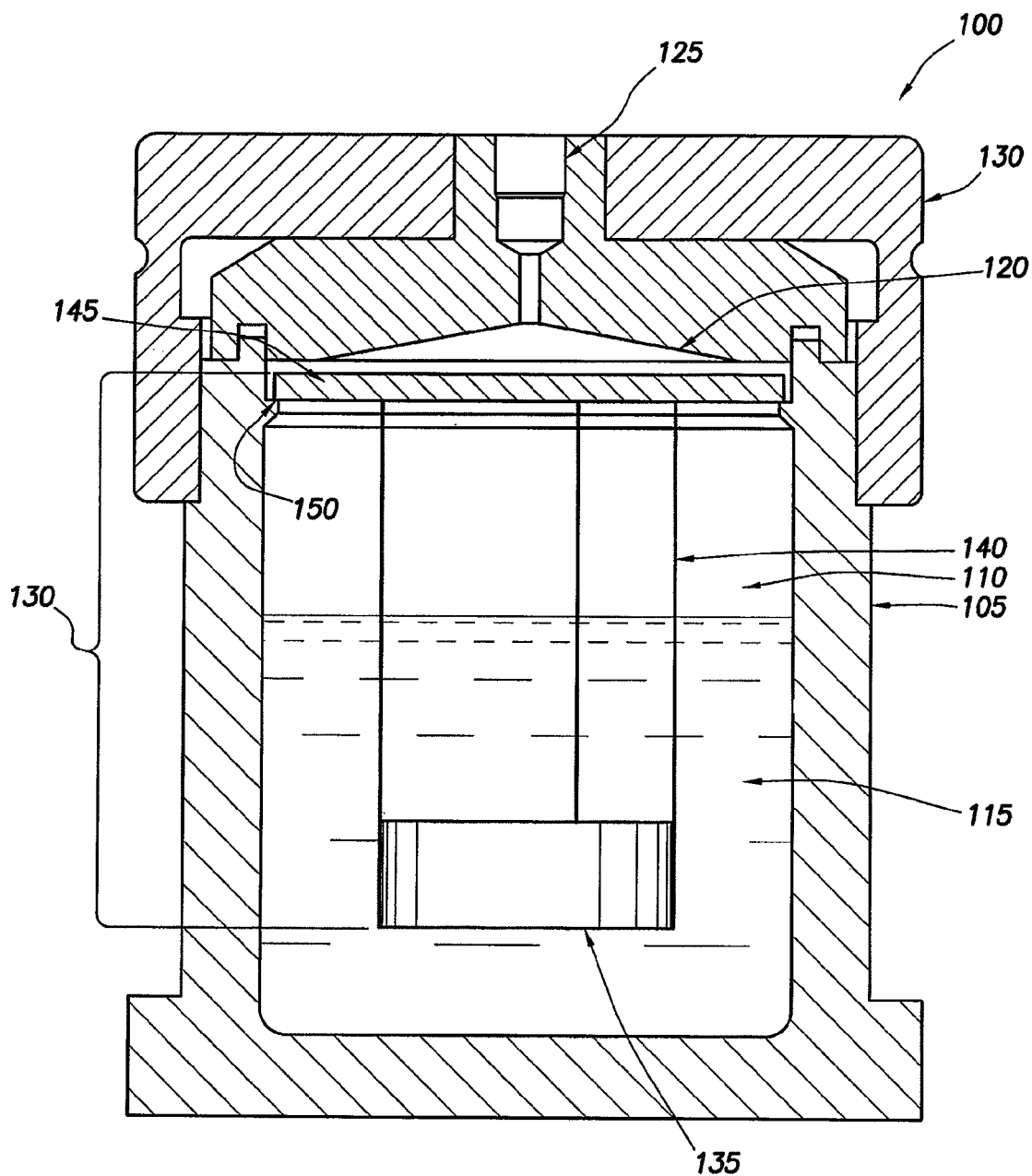
FIG. 1 is a diagram of a testing arrangement, in accordance with certain embodiments of the present disclosure.

FIG. 1 is a diagram of a testing arrangement 100, in accordance with certain embodiments of the present disclosure. The testing arrangement 100 may include a container 105, which, by way of example without limitation, may include a fluid aging cell. The container 105 may include a cavity 110 to receive and contain a fluid 115. The fluid 115 may be any suitable type of fluid, such as a drilling fluid, for which a determination of shear strength, gel strength, or other property is desirable.

The testing arrangement 100 may include a suspension assembly 130. The suspension assembly 130 may include a suspended member 135. In various embodiments, the suspended member 135 may be one or more of a shearometer tube, a cylinder that may be hollow, solid, closed, or open, and a non-cylindrical structure having any suitable geometry.

The container 105 may include a lid 120. The lid 120 may be removably connected to the container 105. The lid 120 may maintain a seal in a groove 121. The groove 122 may include an o-ring (not shown) to facilitate the seal. The lid 120 may be held or supported by the cap 122 in any suitable manner, for non-limiting example, via a threaded connection (not shown). When connected to the container 105, the lid 120 may seal the cavity 110.

A pressurization line 125 may be coupled to the lid 120 for pressurizing and venting the cavity 110 through a pathway 126 through the lid 120. Any suitable pressurization and venting control device or combination of devices (not shown), including but not limited to a pressurization pump, may be coupled to the pressurization line 125 and/or the lid 120 to pressurize and vent the cavity 110. In certain embodiments, the pressurization line 125 may be detachable at the lid 120.

Figure 1A:
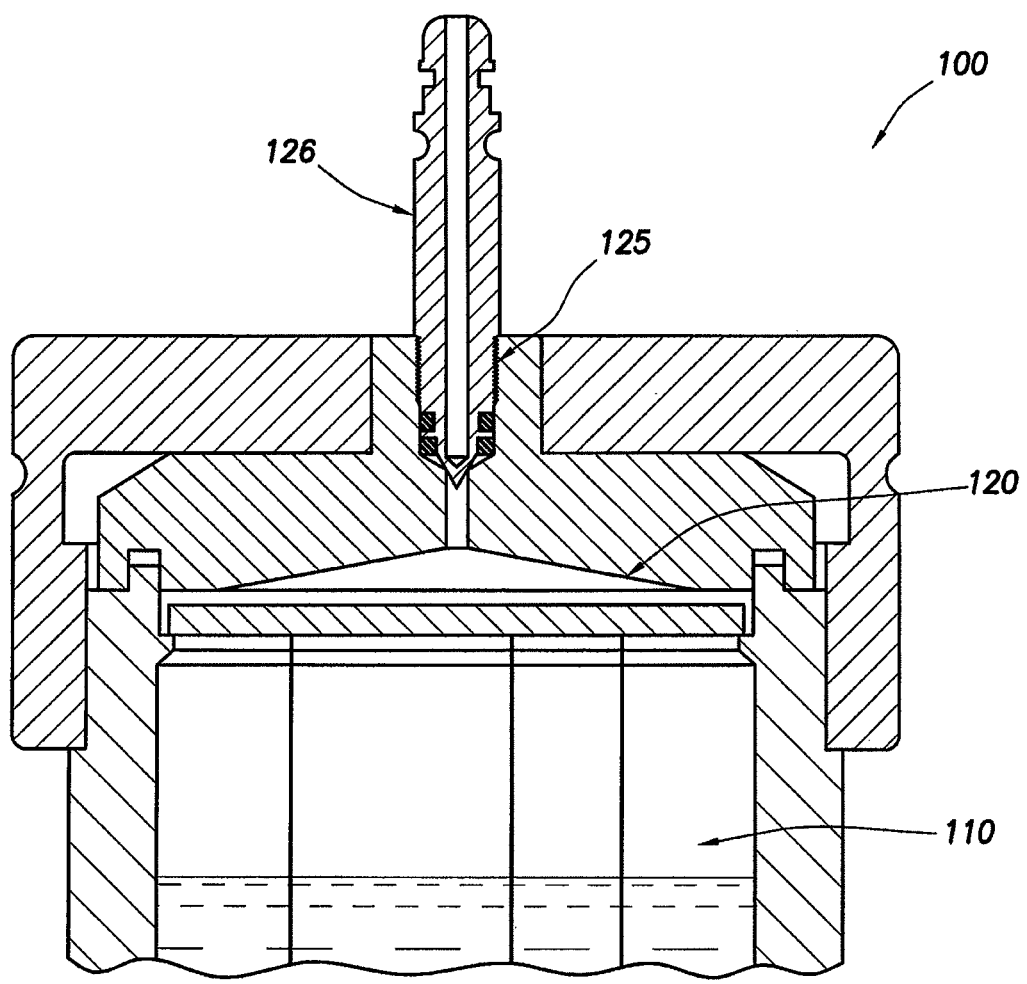
FIG. 1A is a diagram of a testing arrangement where the pressurization line may include a valve stem or other device that allows closure of the pressurization line, in accordance with certain embodiments of the present disclosure.

FIG. 1A is a diagram of a testing arrangement 100 where the pressurization line 125 may include a valve stem 126 or other device that allows closure of the pressurization line 125, in accordance with certain embodiments of the present disclosure. By way of non-limiting example, the valve stem 126 may be a metal to metal pressurizing valve stem that allows pressurization of the cavity 110 through the lid 120 via a pressurization hose (not shown) coupled to the valve stem 126.

Referring again to FIG. 1, certain embodiments may include a cap 122 to further secure the lid 120 and container 105. The cap 122 may be formed to fit over the lid 120 and a portion of the container 105, such as a lip of the container. The cap 122 may function as a safety lock, keeping the lid 120 secure when the cavity 110 is pressurized.

The suspension assembly 130 may include one or more suspenders 140 coupled to the suspended member 135. The suspension assembly 130 may further include a crosspiece 145 coupled to the suspenders 140. The crosspiece 145 may be sized to engage the container 105 at an upper portion of the container 105. As in the non-limiting example depicted, the crosspiece 145 may span a diameter of the container 105 and may be adapted to engage an interior retaining lip or catch 150 of the container 105 at an upper portion of the container 105. With crosspiece 145 seated against the catch 150, the crosspiece 145 may support the one or more suspenders 140 and the suspended member 135 within the cavity 110. The suspenders 140 may be any suitable connectors to suspend the suspended member 135 from the crosspiece 145. By way of example without limitation, the suspenders 140 may include wires, cables, bars, or any other type of suspending member. With the fluid 115 in the cavity 110, the suspended member 135 may be submerged in the fluid 115. In various embodiments, the suspension assembly 130 may be adapted so that the suspended member 135 is resting on a bottom of the cavity 110, near the bottom of the cavity 110, or in any suitable off-bottom position when the crosspiece 145 is seated against the catch 150. The submerged, resting position of the suspended member 135 may correspond to a starting position for the suspended member 135 in a testing process. In the non-limiting examples depicted, the elements of the testing arrangement 100 may be variously composed of any materials suitable to a given application and, for non-limiting example, may include aluminum, other metals, alloys, non-corrosive metals, plastics, composites, etc.

Figure 2A:
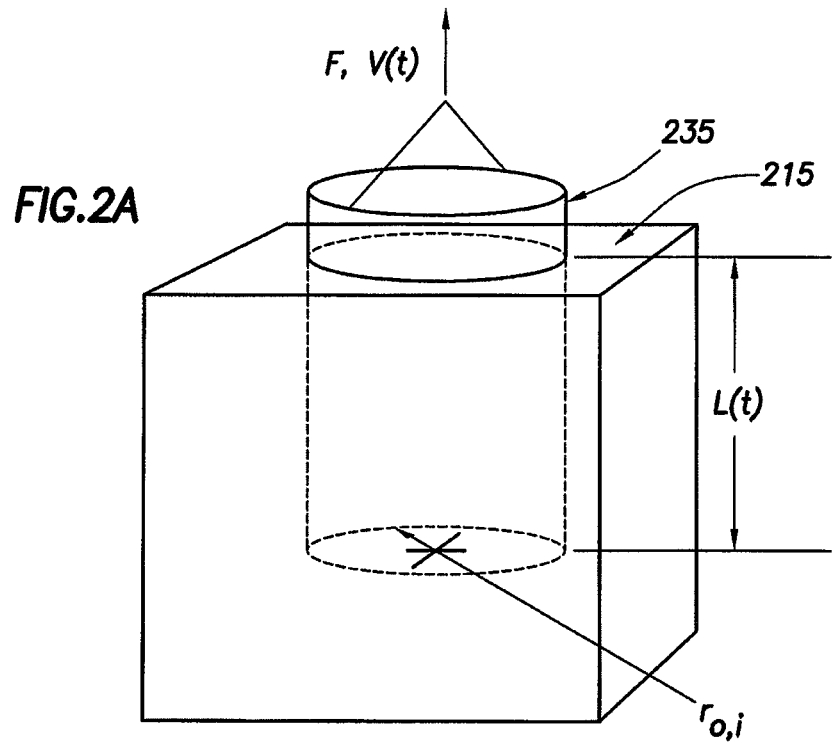
FIG. 2A shows an example of a suspended member in a fluid, in accordance with certain embodiments of the present disclosure.

FIG. 2A shows an example of a suspended member 235 submerged in a fluid 215 and coupled to a suspension assembly 230, in accordance with certain embodiments of the present disclosure. In the example depicted, the suspended member 235 is a tube. A corresponding shear strength and/or gel strength $\sigma(t)$ may be indicated by the following Equations (1) and (2).

$$\sigma(t) = \frac{F(t) - W(t) - Vis(t) - E(t)}{2\pi(r_o + r_i)L_o} \quad \text{Equation (1)}$$

where:
F(t)=a measured force with respect to time;
W(t)=a measured force or weight of the suspension assembly 130;
Vis(t)=a measured force due to viscous effects on the suspended member 135;
E(t)=a measured force due to edge effects on the suspended member 135;
$r_i$=an inner radius of the suspended member 135;
$r_o$=an outer radius of the suspended member 135; and
$L_o$=a length of the suspended member 135.

Figure 2B:
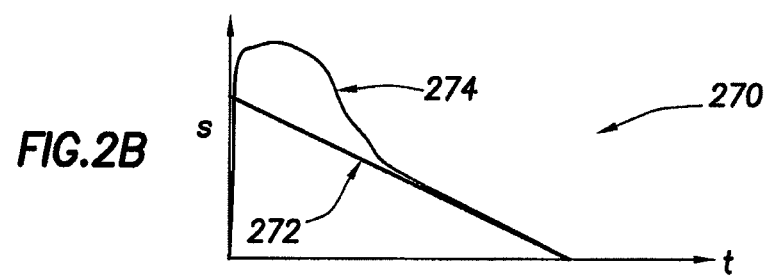
FIG. 2B shows a graph corresponding to an example controlled rate mode of operation, in accordance with certain embodiments of the present disclosure.

FIG. 2B shows a graph 270 corresponding to an example controlled rate mode of operation, in accordance with certain embodiments of the present disclosure. In this mode of operation, the velocity V(t) of the suspended member 235 may be held constant and the suspended member 135 may remain completely immersed in the fluid 115 during the test. The x-axis corresponds to time; the y-axis corresponds to shear stress. The response 274A corresponds to an exemplary combined viscous, gel, weight and edge effect response, where the 274B response corresponds to a steady state response without the initial gel structure. Responses 274A and 274B may be used to calculate the gel response using the following:

$$\text{gel} = \frac{F_{peak} - F_{SS}}{2\pi(r_o + r_i)L_o} \quad \text{Equation (2)}$$

where:
gel=gel strength;
$F_{peak}$=peak force measurement from the 274A response; and
$F_{ss}$=steady state force from 274B.

Figure 2C:
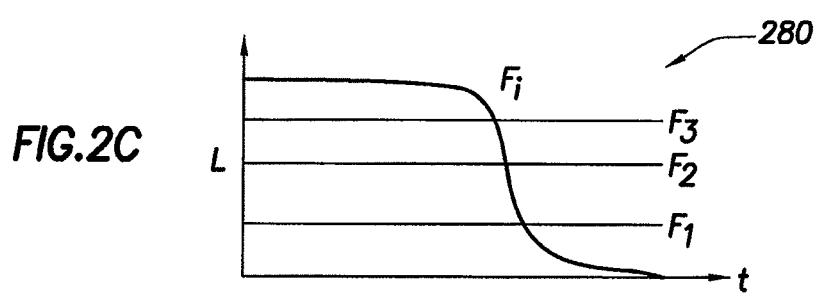
FIG. 2C shows a graph corresponding to an example controlled stress mode of operation, in accordance with certain embodiments of the present disclosure.

FIG. 2C shows a graph 280 corresponding to an example controlled stress mode of operation, in accordance with certain embodiments of the present disclosure. A displacement line 284 in reference to displacement and time axes corresponds to a displacement of the suspended member 235 in the fluid 215. A stress line 284 in reference to stress and time axes axis corresponds to a stress level corrected for an initial weight of the system. In this mode of operation, the force F(t)

pulling the suspended member 235 may be repeatedly held constant for a time and then increased, as indicated by the non-limiting example of stress line 282. The time axis corresponds to the time of the process for stress and displacement. The stress level, as indicated by the non-limiting example of 286, at the first measured displacement may correspond to the gel strength.

Figure 3:
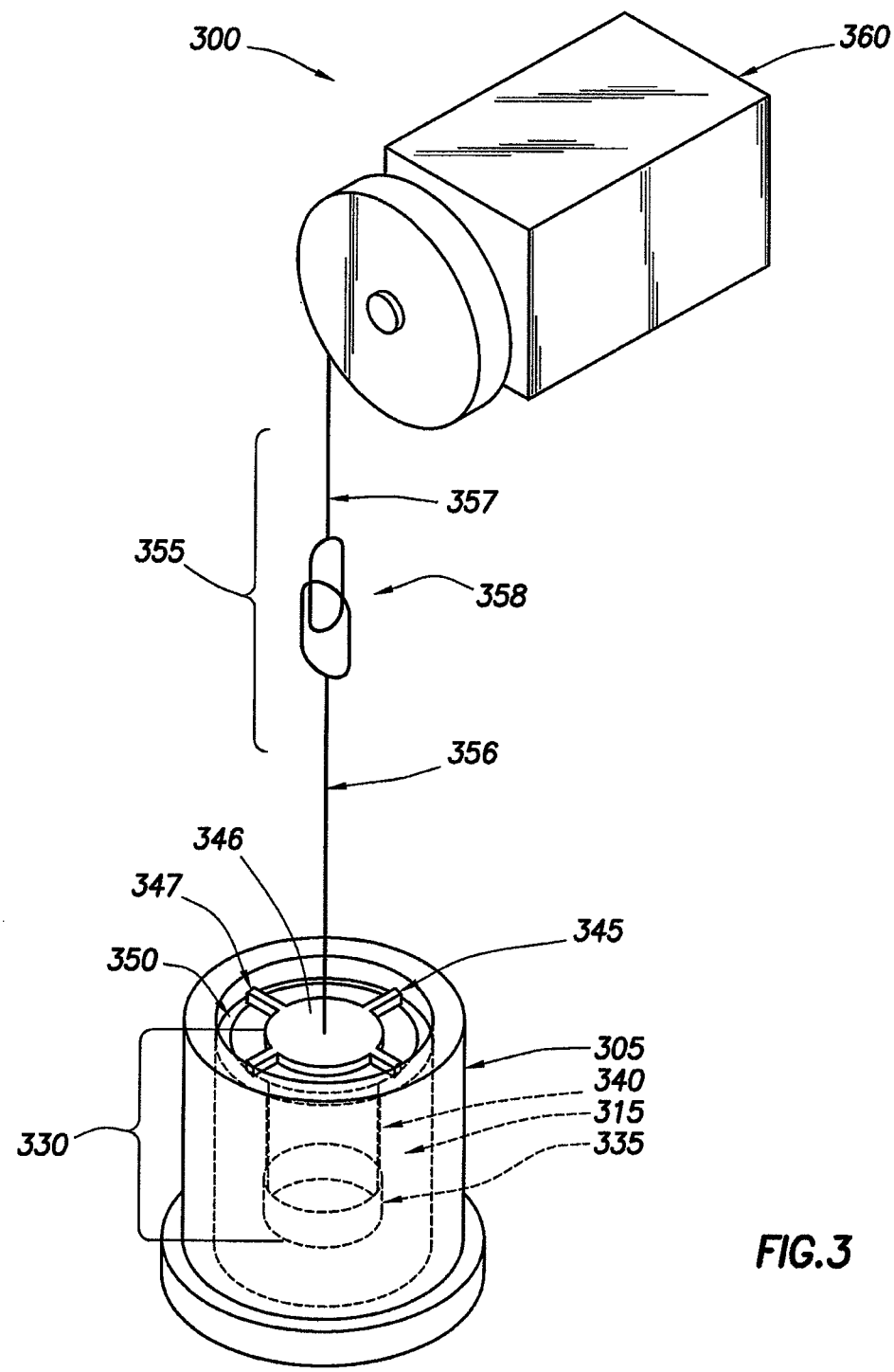
FIG. 3 shows a testing arrangement, in accordance with certain embodiments of the present disclosure.

FIG. 3 shows a testing arrangement 300, in accordance with certain embodiments of the present disclosure. The testing arrangement 300 may include a container 305, a fluid 315, a suspension assembly 330, a link 355, and a control device 360. The container 305 is depicted in FIG. 3 with lid and/or cap removed. The suspension assembly 330 may include a suspended member 335, one or more suspenders 340, and a crosspiece 345 in coupled arrangement. The suspended member 335 and suspenders 340 may correspond to the suspended member 135 and suspenders 140 of the testing arrangement 100. As depicted, the crosspiece 345 may include a central portion 346 coupling the link 355 and the suspenders 340. Extensions 347 may extend from the central portion 346 to a catch 350 at an upper portion of the container 305.

The link 355 may be removably attached or fixedly attached to the suspension assembly 330 in any suitable manner. The link 355 may couple the suspension assembly 330 and the control device 360. The link 355 may be removably attached and/or fixedly attached to the suspension assembly 330 and the control device 360 in any suitable manner. The link 355 may include any suitable connector and may include, but not be limited to, one or more wires, cables, ropes, chains, straps, rods, etc. In certain embodiments, the link 355 may include two portions 356 and 357 connected via a coupling 358. The coupling 358 may include any suitable means of connecting the two portions 356 and 357. By way of example without limitation, the coupling 358 may include one or more snap hooks, eyelets, quick links, shackles, swivels, clips, hooks, rings, buckles, binders, etc.

The control device 360 may be configured to apply a plurality of forces to the link 355 and the suspension assembly 330. Certain embodiments of the control device 360 may include a winch or other device that may include a wheel mounted on a shaft for rotational movement to wind up, release, and otherwise adjust the tension of the link 355. Certain embodiments of the control device 360 may include a cherry picker or other device adjust the tension of the link 355. The control device 360 may include a motor drivingly coupled to the shaft. The control device 360 may be configured so that the tension on the link 355 is adjustable. In certain embodiments, the control device 360 may be a manually operated torque wrench or other manually operated device to apply a pulling force on the link 355 and the suspension assembly 330.

Certain embodiments of the control device 360 may include a sensor to measure the tension on the link 355 and thus indicate a force applied to the suspended member 335. In certain embodiments, the control device 360 may further include a display, gauge, or other indicator to indicate amounts of tension on the link 355 in real time or otherwise for an operator to observe. For non-limiting example, the sensor may include a torque sensor and/or a strain gauge assembly.

Figure 4A:
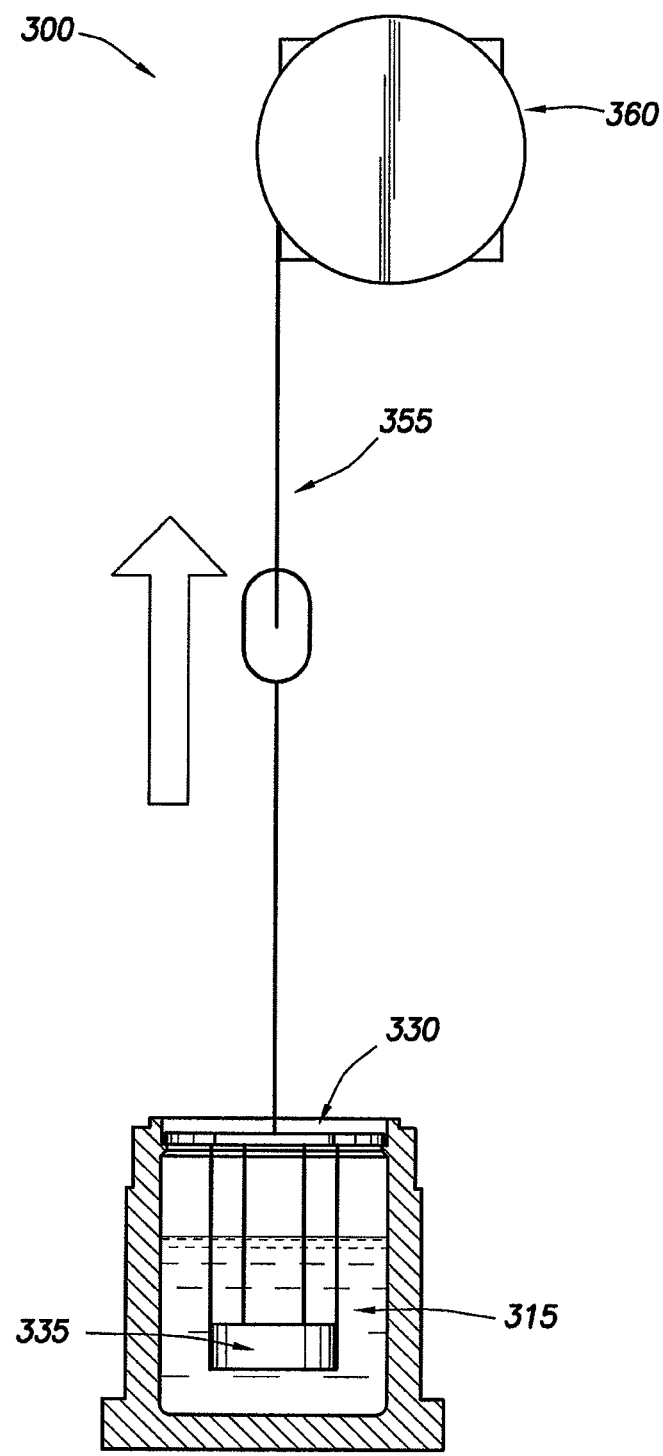
FIGS. 4A and 4B show the testing arrangement of FIG. 3 in different stages of an example testing method, in accordance with certain embodiments of the present disclosure.
Figure 4B:
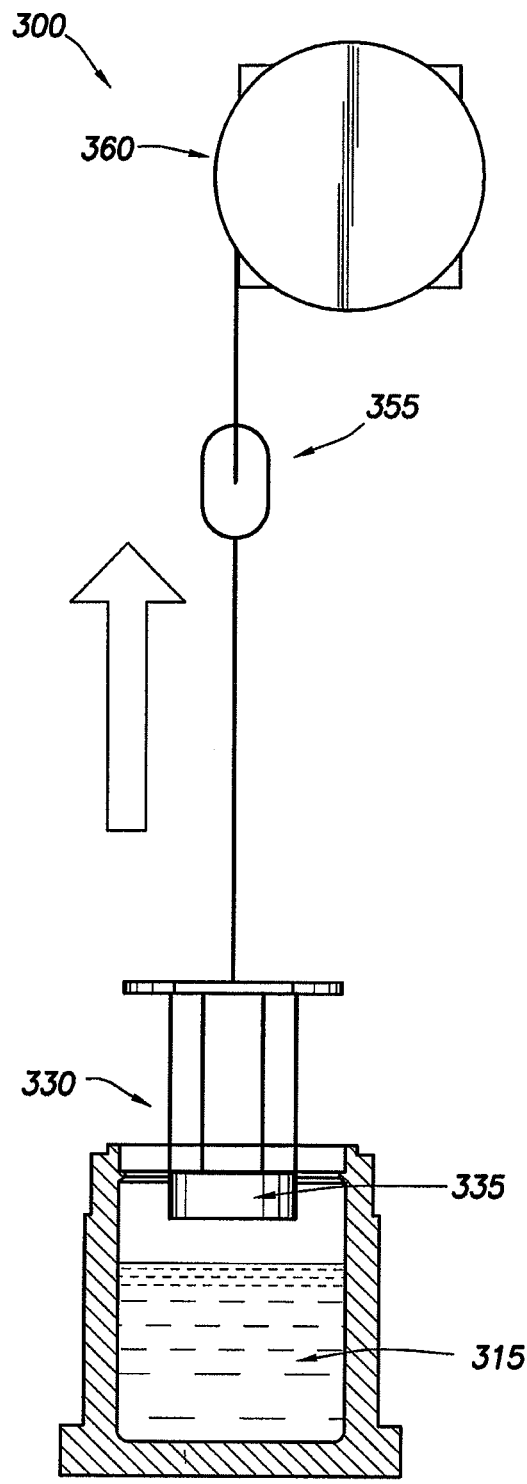

As illustrated in FIG. 4A, with the control device 360, an operator may apply a first force to the coupled link 355 and suspension assembly 330 after the suspended member 335 has been submerged in the fluid 315 for an appropriate amount of time. If the suspension assembly 330, and more specifically the suspended member 335, does not move, a second force greater than the first force may be applied. And the operator may iteratively increase the force applied to the suspended member 335 until reaching a force sufficient to cause the suspended member 335 to move. The operator may manually stop the movement of the suspended member 335 at any suitable point. For example, as illustrated in FIG. 4B, the movement of the suspended member 335 may be stopped after the suspended member 335 has exited the fluid 335. The operator may measure a time corresponding to the movement of the suspended member 335. One or more of the force sufficient to cause the suspended member 335 to move and the time corresponding to the movement may indicate a property of the fluid 315. By way of example without limitation, a determination of a shear strength and/or a gel strength of the fluid 315 may be made based, at least in part, on one or more of that force and that time.

Certain embodiments of the control device 360 may be configured for lessened operator involvement to test the fluid 315. Certain embodiments may be carried out in conjunction with a computer having a processor, a memory, and storage. For example, the control device 360 may include or be coupled to a processor, a memory, and storage to facilitate one or more of the features described herein. Instructions for relating to one or more features described herein may be stored in software run on the computer. The control device 360 may include or be coupled to any instrumentality or aggregate of instrumentalities operable to compute, classify, process, transmit, receive, retrieve, originate, switch, store, display, manifest, detect, record, reproduce, handle or utilize any form of information, intelligence or data for testing purposes. The control device 360 may include or be coupled to random access memory (RAM), one or more processing resources such as a central processing unit (CPU or processor) or hardware or software control logic, read-only memory (ROM) and/or other types of nonvolatile memory. The control device 360 may include or be coupled to one or more disk drives, one or more network ports for communication with external devices as well as various input and output devices, such as a keyboard, a mouse and a video display.

The control device 360 may be configured to receive one or more input parameters, and may be include one or more sensors configured to provide signals relating to the one or more input parameters. The control device 360 may take into account one or more of an elevation of the suspended member 335, the position of the suspended member 335, and the tension of the link 355. The control device 360 may utilize one or more of a feedback control loop and a feed forward control function.

As part of a testing process initiated by the operator, the control device 360 may automatically begin testing after the suspended member 335 has been submerged in the fluid 315 for a predetermined amount of time. The control device 360 may be configured to automatically apply a plurality of forces on the link 355 and suspension assembly 330. The forces may be increased by any suitable force increment over any suitable time increment. Thus, the control device 360 may apply a series of increasing forces until the suspended member 335 moves, at which point the force sufficient to move the suspended member 335 may be maintained for a time.

In certain embodiments, the control device 360 may measure an amount of time during which the suspended member 335 travels a particular distance corresponding to a particular pulling force applied. The control device 360 may automatically stop pulling the suspended member 335 at an appropriate point. In certain embodiments, the control device 360 may stop pulling the suspended member 335 based, at least in part, on a predetermined distance that the suspended member 335 should travel, a predetermined length of the link 355 that should be wound, and/or a predetermined rotational parameter of the wheel/shaft. In certain embodiments, the control device 360 may stop pulling the suspended member 335 based, at least in part, on a force differential resulting from the suspended member 335 exiting the fluid 315.

In certain embodiments, the control device 360 may calculate a property of the fluid 315 based, at least in part, on one or more of the force sufficient to cause the suspended member 335 to move and the time corresponding to the movement. In certain embodiments, the control device 360 may provide a determination of a shear strength and/or a gel strength of the fluid 315 based, at least in part, on one or more of that force and that time. Certain embodiments of the control device 360 may record any desired data associated with the testing process.

Figure 5:
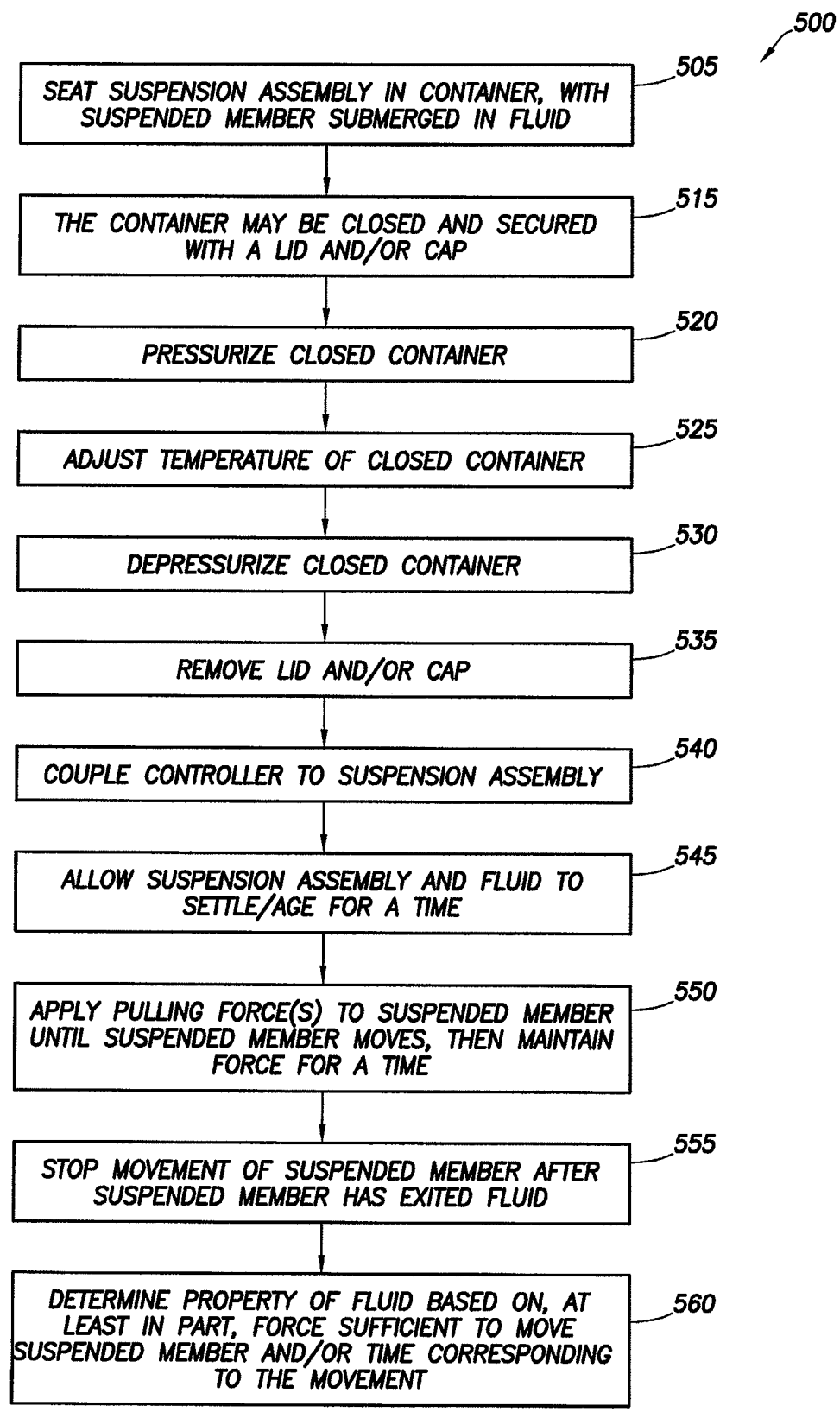
FIG. 5 depicts a flow diagram for an example testing method, in accordance with certain exemplary embodiments of the present disclosure.

FIG. 5 depicts a flow diagram for an example testing method 500, in accordance with certain exemplary embodiments of the present disclosure. Teachings of the present disclosure may be utilized in a variety of implementations. As such, the order, combination, and/or performance of the steps comprising the method 500 may depend on the implementation chosen.

According to one example, the testing method 500 may begin at step 505. At step 505, a test fluid may be introduced into a container. At step 510, a suspension assembly may be seated in the container, with a suspended member submerged in the fluid and in any suitable on-bottom or off-bottom position. At step 515, the container may be closed and secured with a lid and/or cap. Prior to the closing, portion of a link that may be coupled to the suspension assembly, such as portion 356, may be detached or collapsed/coiled up on top of the suspension assembly. At step 520, the closed container may be pressurized. At step 525, the temperature of closed container may be adjusted. For non-limiting example, the closed container may be placed in an oven to be heated for a time. In preparation for placement in the oven, a pressurization line extending from the lid and/or cap may either be detached or collapsed/coiled up on top of the container. At step 530, the closed container may be depressurized, for example, through the pressurization line. At step 535, the lid and/or cap may be removed. At step 540, a controller may be coupled to the suspension assembly via the link. At step 545, the suspension assembly and fluid may be allowed to settle/age for a time. At step 550, one or more pulling forces may be applied to the suspension assembly until the suspended member moves, at which point the force sufficient to move the suspended member may be maintained for a time. At step 555, the movement of the suspended member may be stopped after the suspended member has exited the fluid. At step 560, a property of the fluid may be determined based, at least in part, on one or more of the force sufficient to cause the suspended member to move and the time corresponding to the movement.

In alternative embodiments according to the present disclosure, the testing arrangement 100 may be modified to allow for testing performed at high temperature and/or under pressure. The cavity 110 may be heated and/or pressurized to any suitable extent. The suspension assembly 130, including the crosspiece 145, the suspenders 140A, and the suspended member 135, may be pulled through the fluid 115 while a desired temperature and/or pressure is maintained. By way of example without limitation, in such embodiments, the control device 360 may be contained in the testing arrangement 100 and may be adapted for operation at the desired temperature and/or pressure, or isolated therefrom. In certain embodiments, the control device 360 may be connected magnetically through the walls container 105.

Accordingly, certain embodiments according to the present disclosure, as compared to conventional means, may allow for significantly increased reliability, ease of use, repeatability and accuracy. Certain embodiments may allow for multiple simultaneous measurements with multiple units. Certain embodiments may be portable and adaptable to different testing setup areas.

Even though the figures depict embodiments of the present disclosure in a particular orientation, it should be understood by those skilled in the art that embodiments of the present disclosure are well suited for use in a variety of orientations. Accordingly, it should be understood by those skilled in the art that the use of directional terms such as above, below, upper, lower, upward, downward, higher, lower, and the like are used in relation to the illustrative embodiments as they are depicted in the figures, the upward direction being toward the top of the corresponding figure and the downward direction being toward the bottom of the corresponding figure.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. Also, the terms in the claims have their plain, ordinary meaning unless otherwise explicitly and clearly defined by the patentee. The indefinite articles "a" or "an," as used in the claims, are defined herein to mean one or more than one of the element that the particular article introduces; and subsequent use of the definite article "the" is not intended to negate that meaning.

What is claimed is:

1. An apparatus to test a property of a fluid, the apparatus comprising:
    a container, the container having a wall forming a cavity, wherein the wall retains a fluid within the cavity;
    a catch protruding from the wall of the container, wherein the catch is adjacent to the cavity;
    a suspended member to be submerged in the fluid;
    a control device coupled to the suspended member and configured to pull the suspended member through at least a portion of the fluid to test a property of the fluid; and
    a crosspiece adapted to seat against the catch and coupled to the suspended member so that the suspended member is disposed within the cavity when the crosspiece is seated against the catch.

2. The apparatus of claim 1, wherein the control device is configured to apply a plurality of pulling forces to the suspended member.

3. The apparatus of claim 1, wherein the control device is configured to indicate a force sufficient to move the suspended member.

4. The apparatus of claim 1, wherein the control device is configured to determine a property of a fluid in the container based, at least in part, on a force sufficient to move the suspended member through at least a portion of the fluid.

5. The apparatus of claim 1, wherein the control device is configured to measure a time corresponding to a movement of the suspended member over a predetermined distance.

6. The apparatus of claim 1, wherein the control device is configured to determine a property of a fluid in the container based, at least in part, on a time corresponding to movement of the suspended member over a predetermined distance.

7. The apparatus of claim 1, wherein the control device is configured to move the suspended member a predetermined distance.

8. The apparatus of claim 1, wherein the control device is configured to stop pulling the suspended member after the suspended member exits the fluid in the container.

9. The apparatus of claim 1, wherein the suspended member comprises a cylinder.

10. The apparatus of claim 1, wherein the property is a shear strength or a gel strength.

11. An apparatus to test a property of a fluid, the apparatus comprising:
   a container comprising a wall forming a cavity, wherein the wall retains a fluid within the cavity;
   a lid removably connected to the container, wherein the lid seals the cavity;
   a pressurization line coupled to the lid, wherein the pressurization line is operable to at least one of pressurize and vent the cavity;
   a catch protruding from the wall of the container, wherein the catch protrudes from a portion of the wall of the container disposed within the cavity;
   a crosspiece adapted to span at least a portion of the cavity, wherein the crosspiece is adapted to seat against the catch; and
   a suspended member coupled to the crosspiece so that the suspended member is disposed within the cavity when the crosspiece is seated against the catch and so that the suspended member is pulled through at least a portion of the cavity when the crosspiece is lifted from the catch.

12. The apparatus of claim 11, further comprising:
   a control device coupled to the crosspiece to apply a plurality of pulling forces to the crosspiece.

13. The apparatus of claim 12, wherein the control device is configured to indicate a force sufficient to move the suspended member.

14. The apparatus of claim 12, wherein the control device is configured to determine a property of a fluid in the container based, at least in part, on a force sufficient to move the suspended member through at least a portion of the fluid.

15. The apparatus of claim 12, wherein the control device is configured to measure a time corresponding to a movement of the suspended member over a predetermined distance.

16. The apparatus of claim 15, wherein the control device is configured to determine a property of a fluid in the container based, at least in part, on the time corresponding to the movement of the suspended member over the predetermined distance.

17. The apparatus of claim 12, wherein the control device is configured to move the suspended member a predetermined distance.

18. A method of testing a property of a fluid, the method comprising:
   introducing a fluid into a container, the container comprising:
      a wall forming a cavity, wherein the wall retains a fluid within the cavity;
      a lid removably connected to the container, wherein the lid seals the cavity;
      a pressurization line coupled to the lid, wherein the pressurization line is operable to at least one of pressurize and vent the cavity;
      a catch protruding from the wall of the container, wherein the catch protrudes from a portion of the wall of the container disposed within the cavity; and
      a crosspiece adapted to seat against the catch;
   disposing at least a portion of a suspended member in the fluid, wherein the suspended member is coupled to the crosspiece; and
   pulling the suspended member through at least a portion of the fluid; and
   determining a property of the fluid based, at least in part, on one of a force sufficient to cause the suspended member to move and a time corresponding to the movement of the suspended member.

19. The method of claim 18, further comprising:
   coupling a control device to the suspended member, wherein the control device is configured to apply a plurality of pulling forces to the suspended member;
   wherein the step of pulling the suspended member is performed, at least in part, with the control device.

* * * * *